United States Patent [19]

Cummings

[11] 4,266,958

[45] May 12, 1981

[54] SIMULTANEOUS COOLING AND REMOVAL OF WATER FROM HYDROCARBON GAS MIXTURES

[75] Inventor: Donald R. Cummings, Cheltenham, England

[73] Assignee: Dut Pty Limited, Sydney, Australia

[21] Appl. No.: 56,724

[22] Filed: Jul. 11, 1979

[30] Foreign Application Priority Data

Jul. 17, 1978 [GB] United Kingdom ............... 30085/78

[51] Int. Cl.³ .................................................. F25J 1/02
[52] U.S. Cl. ......................................... 62/20; 62/17; 62/11; 62/54; 62/55; 585/833; 208/106
[58] Field of Search ................... 62/20, 17, 11, 55, 54, 62/52, 45; 585/833, 834

[56] References Cited

U.S. PATENT DOCUMENTS

| | | | |
|---|---|---|---|
| 3,034,309 | 5/1962 | Muck | 62/9 |
| 3,886,757 | 6/1975 | McClintock et al. | 62/20 |

FOREIGN PATENT DOCUMENTS 2105304 7/1972 Fed. Rep. of Germany .
1415910 9/1965 France .

Primary Examiner—Norman Yudkoff
Attorney, Agent, or Firm—Browdy & Neimark

[57] ABSTRACT

Dehydration of a gaseous hydrocarbon mixture containing water, using methanol as the dehydration agent, and recovery of a condensed fraction of said mixture can be achieved simultaneously and with improved use of the methanol and improved separation of the mixture, and in apparatus which can be employed on an installation such as a tanker ship which is liable to movement and/or tilting, by chilling a gaseous composition comprising the water-containing mixture and methanol in passageway 18 of a reflux exchanger 6 in which condensed liquids flow downwards in direct contact with the rising gas and are collected in a gas-/liquid separator 4 from which a condensed hydrocarbon phase and an aqueous phase can be recovered separately; dehydrated gas being recovered from the top of the passageway.

24 Claims, 6 Drawing Figures

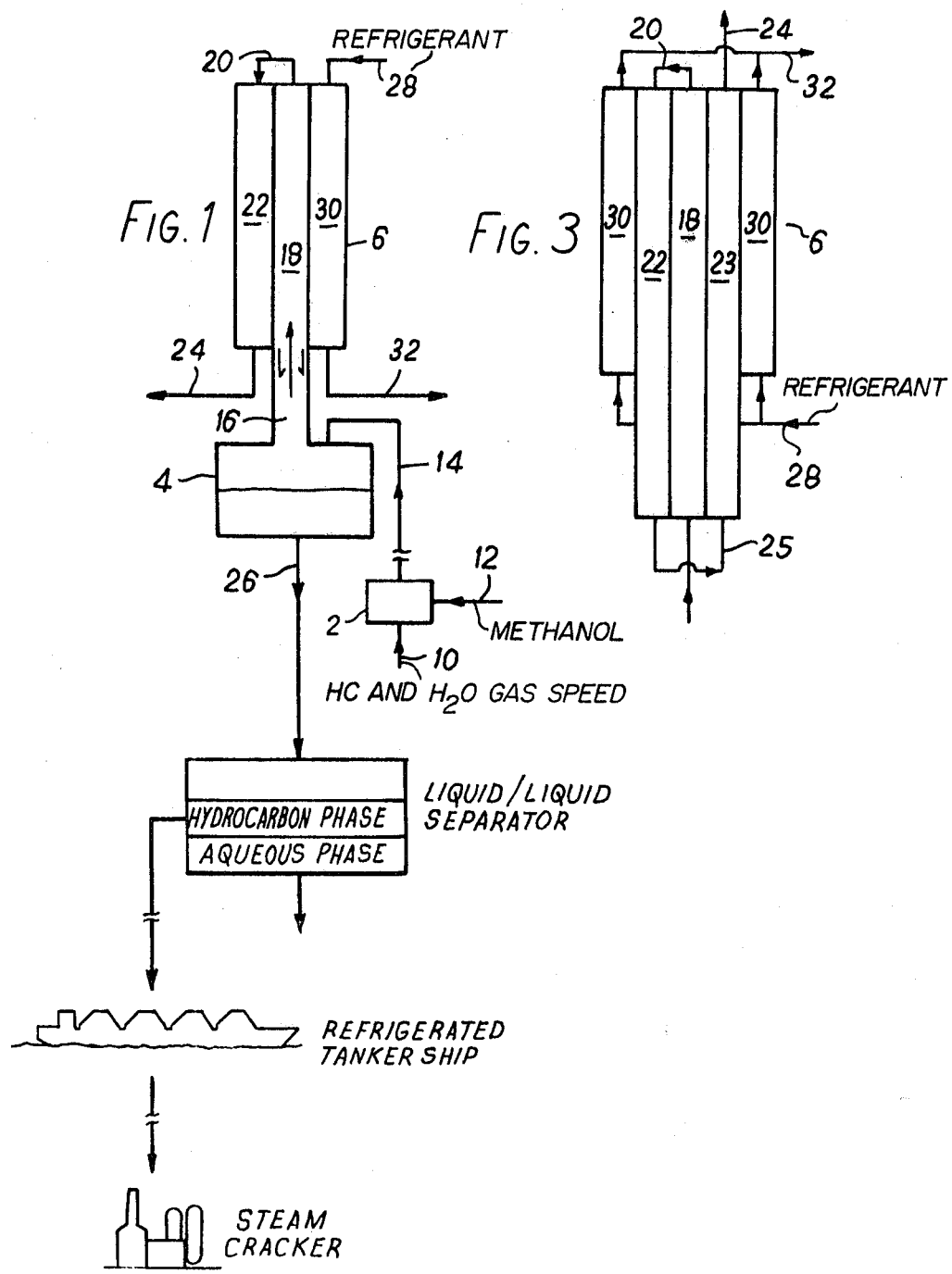

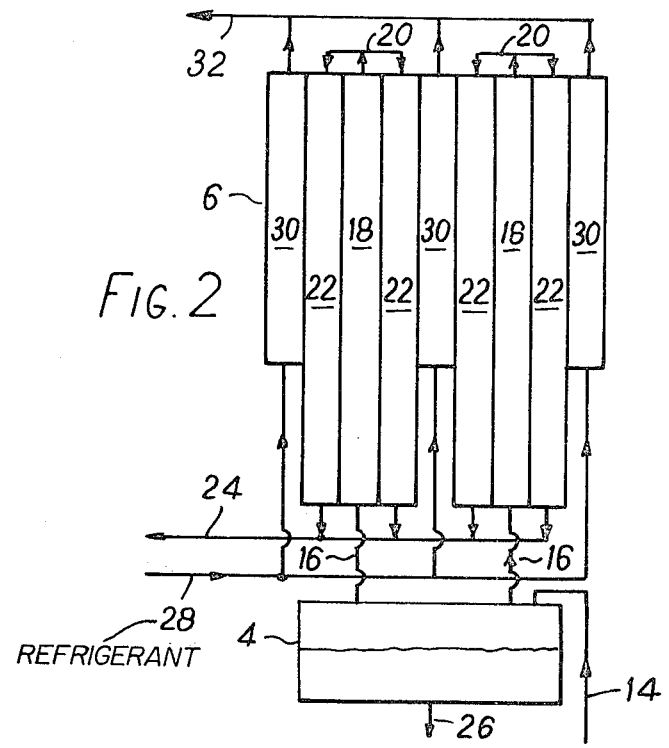

SIMULTANEOUS COOLING AND REMOVAL OF WATER FROM HYDROCARBON GAS MIXTURES

This invention relates to the simultaneous chilling and dehydration of water-containing gaseous hydrocarbon mixtures to which methanol has been added as a dehydrating agent.

When water-containing gaseous hydrocarbon mixtures are to be cooled to low temperatures and in particular to temperatures below those at which ice and/or hydrates of the hydrocarbons are formed, e.g. in order to facilitate the condensation of a part or all of the gas, it is essential either to dehydrate the mixture or to add a hydrate suppression agent/water absorbent such as methanol or a glycol. Otherwise the water in the gaseous mixture will freeze or form solid hydrates with the hydrocarbons during the cooling step.

A conventional method of using methanol for this purpose involves adding it in gaseous form to the mixture, cooling the resultant methanol-containing composition whereby to form a hydrocarbon-immiscible liquid aqueous phase containing methanol and water absorbed from the hydrocarbon mixture and separating the aqueous phase from the hydrocarbon phase. The temperature to which a gaseous hydrocarbon mixture can be cooled by conventional manner, however, is limited by the degree of condensation of the hydrocarbon mixture that can be tolerated. For example, for a binary mixture, in particular, the temperature to which it can be cooled must exceed the boiling point of the lighter hydrocarbon if separation of the mixture is desired.

The present invention provides a method which permits the cooling of binary gaseous hydrocarbon mixtures down even to the liquefaction temperature of the lighter component while still achieving separation of the two components, thereby lowering the permissible minimum temperature for the cooling step as compared with conventional processes and thus permitting (a) lower methanol losses in the gas phase, (b) improved hydrocarbon separation and (c) simultaneous dehydration of the mixture and stabilisation of the hydrocarbon liquid separated out by the cooling process. Similar benefits are possible with hydrocarbon mixtures containing three or more components.

The method of the present invention also permits a reduction in the amount of methanol required for a given final cooling temperature, thus permitting a higher water/methanol ratio in the aqueous layer which separates out which in turn reduces the solubility of the methanol in the hydrocarbon and therefore the loss of methanol in the hydrocarbon phase. Where the methanol is employed in the form of an aqueous solution of methanol, this in turn permits the use of more dilute solutions than would otherwise be possible.

A further advantage of the method is that it may be carried out in apparatus the efficient operation of which is relatively unaffected by movement or moderate inclination or tilting of the equipment and is therefore particularly suitable for use e.g. on board ships, barges, moving platforms and tower loading buoys.

In accordance with this invention the method comprises chilling a gaseous composition comprising a water-containing gaseous hydrocarbon mixture and a controlled or known concentration of methanol vapour to a temperature which lies below the ice or hydrate formation temperature of said water-containing hydrocarbon mixture by passing it upwards in indirect heat exchange relationship with a coolant through a heat exchanger in which the composition is cooled and liquids condensed therefrom flow downwards in a counter-current fashion in contact with the rising composition being cooled, the temperature of the rising composition and of the down flowing condensed liquids in the exchanger decreasing from bottom to top of the heat exchanger, and recovering dehydrated gaseous hydrocarbon from the top of the exchanger and an aqueous condensate from the bottom.

Where partial condensation of the hydrocarbon mixture occurs as a result of the chilling, the condensate recovered from the base of the exchanger will comprise an aqeuous phase and a condensed hydrocarbon phase which can readily be separated from the aqueous phase.

The condensed hydrocarbon in contact with the aqueous phase will be saturated with water and methanol in accordance with the ternary phase equilibria of the hydrocarbon/water/methanol system at that temperature. The liquid hydrocarbon may be separated and withdrawn as such or alternatively it may be separated and further chilled in order to further reduce its water/methanol content or it may be withdrawn and treated in accordance with our co-pending UK Application No. 30086/78 to reduce its water and methanol content.

Alternatively the hydrocarbon and aqueous layers may be both chilled and separated at a lower temperature to further reduce the water and methanol content of the hydrocarbon layer.

Gaseous hydrocarbon mixtures to which the process of the invention will generally be applied will predominate in $C_1$ to $C_4$ hydrocarbons and include, for example, natural gas streams containing some $C_2$ and heavier hydrocarbons, gases associated with naturally occurring oil (associated gases), end gases from oil refining and gases derived from cracking, hydrocracking, hydrotreating or catalytic reforming of hydrocarbons. Because of the nature of these gaseous hydrocarbon mixtures, the process of the invention will normally be conducted at superatmospheric pressure, usually in the range 50 to 1000 psig, but pressure is not critical to the process.

The gaseous hydrocarbon mixtures may and generally will also include gases other than hydrocarbons. For example, naturally occurring mixtures will include inert gases such as $N_2$ and He and/or acid gases such as $CO_2$ and $H_2S$, and manufactured gases may also contain $H_2$ and CO.

As the gaseous composition passes upwards through the exchanger and is cooled, the water therein will tend to condense in preference to the methanol, thus increasing the ratio of the methanol to water vapour in the gas and thus as the vapours pass up the heat exchanger the ratio of methanol to water vapour in the gas phase will increase. Likewise the ratio of methanol to water in the liquid phase will also increase as the temperature decreases. Thus, a hydrocarbon/water/methanol gas mixture of given composition may be chilled to a lower temperature than would be possible with the use of conventional heat exchanger arrangements. Alternatively less methanol is required in the wet hydrocarbon gas mixture for a given temperature drop and thus where the methanol is supplied to the wet hydrocarbon in the form of an aqueous solution of methanol, more dilute solutions may be employed thus simplifying methanol recovery in the case where the methanol-containing aqueous phase separated from the hydrocarbon by the chilling step is recycled.

A further advantage is that since the total inventory of methanol and water decreases up the heat exchanger it is possible to permit the temperature of the cold end of the exchanger to drop below that at which ice and or solid hydrates form while still achieving relatively continuous operation with only infrequent warming being required to melt the solids. Moreover, depending on the methanol/water ratio at the cold end of the exchanger, the maximum required temperature for the warming will generally not exceed about $-90°$ C.

Where it is desired to cool the gaseous mixture below $-90°$ C., it may be necessary to withdraw the gas from the heat exchanger before solids formation occurs and contact it with a methanol/water mixture to reduce the methanol/water ratio in the gas to a level such that it is between about 68 and 78%, based on combined weight of methanol and water in the gas, before continuing the cooling.

Where the hydrocarbon mixture is partially condensed in the chilling step, there if preferential condensation of heavier components at the lower, warmer end of the exchanger and also the warm gases at the lower end tend to strip or remove light components from the descending condensed hydrocarbons which then return upwards with the gas to be cooled. In this way the condensed hydrocarbon material contains a much lower percentage of lighter fractions than would be obtained by normal cooling and removal of condensate, and thus stabilization of the condensed hydrocarbon is improved.

If the cooling is effected by passing the composition through the tubes of a shell and tube exchanger, the distribution of liquid throughout the tubes is unaffected by movement or inclination of the tubes and because condensation is taking place on the tube surface the maldistribution of the liquid within each tube is reduced. Thus, using this arrangement enables the process of the invention to be operated satisfactorily e.g. on a ship, floating barge, moving platform or tower loading buoy.

This effect is increased with decrease in tube internal diameter and it is preferred that this dimension be from $\frac{1}{4}$ to $\frac{3}{4}$ inch. Plate and fin exchangers of the kind which can be regarded as the equivalent of shell and tube exchangers in which the gas-processing passageways are vertical or inclined may also be employed.

The cooling for the heat exchanger may be provided by a refrigerant stream which may be gaseous or a boiling liquid. Where it is a boiling liquid, it is preferred that there is a second heat transfer fluid between the refrigerant and the downwardly flowing liquid condensed out of the gas under treatment. This is particularly desirable if the methanol/water ratio in the mixture being fed to the heat exchanger is such that the freezing point of the initially condensed aqueous phase is below that of the boiling refrigerant.

In one preferred embodiment, the chilled gas recovered from the top of the heat exchanger is passed back down the heat exchanger in indirect counter-current heat exchange relationship with the gas being chilled and in passageways lying between the gas being chilled and the passageways carrying the boiling liquid refrigerant. If it is desired to recover the gas from the cold end of the exchanger, the gas may then be passed back up through the heat exchanger in further passageways, and then recovered from the top, or cold end, of the exchanger.

Further rectification of the condensate obtained by the process of the invention can be achieved by passing the gas to be treated in indirect heat exchange relationship with the condensate recovered from the lower or hot end of the heat exchanger before passing the gas into said heat exchanger. This improvement is applicable whether or not partial condensation of the hydrocarbon mixture is effected in the heat exchanger.

Methanol condensed from the chilled gas in the heat exchanger may be recovered and re-incorporated into gas to be treated in the heat exchanger by contacting at least some of the aqueous phase in the condensate recovered from the lower or hot end of the heat exchanger with gas to be fed to the heat exchanger and at a temperature at which at least some of the methanol will be vaporised from the aqueous phase and entrained in the gas.

The invention also provides apparatus for simultaneously cooling and dehydrating a water-containing gaseous hydrocarbon stream, the apparatus including a mixer for mixing methanol with said stream and having inlets for a methanol-containing stream and said hydrocarbon stream and an outlet for the gaseous composition formed by mixing said streams; a heat exchanger having at least a first passageway adapted for generally upward passage therethrough of said composition from an inlet at the bottom to an outlet at the top and generally countercurrent downward passage therein to the inlet of condensate formed in said passageway from said composition and at least a second passageway adapted for passage therethrough of a coolant in indirect heat exchange relationship with said composition in said first passageway to cool said composition as it passes upwards from said inlet to said outlet; means for supplying said composition from said mixer outlet to said heat exchanger passageway inlet; a gas/liquid separator having at least one outlet for liquid collected therein; and conduit means connecting the gas space in said separator with the inlet of said first passageway and adapted to pass gas from said space generally upwardly to said passageway inlet and permit condensate formed in said passageway to fall back from said inlet to said separator.

The invention further provides apparatus for simultaneously cooling and dehydrating a gaseous composition comprising a water-containing hydrocarbon gas mixture and methanol vapour and obtaining a chilled condensate from said gas mixture, e.g. for eventual storage in a cargo space of a tanker, said apparatus comprising a heat exchanger having at least a first passageway adapted for generally upward passage therethrough of said composition from an inlet at the bottom to an outlet at the top and generally countercurrent downward passage therein to the inlet of condensate formed in said passageway from said composition and at least a second passageway adapted for passage therethrough of a coolant in indirect heat exchange relationship with said composition in said first passageway to cool said composition as it passes upwards from said inlet to said outlet, means for supplying said composition to said inlet; a gas/liquid separator; conduit means connecting the gas space in said separator with the inlet of said first passageway and adapted to pass gas from said space generally upwardly to said passageway inlet and permit condensate formed in said passageway to fall back from said inlet to said separator, said separator also having first and second outlets for a hdrocarbon phase and an aqueous phase, respectively, of said condensate; and means for contacting an aqueous stream from said aqueous phase outlet with said water-containing hydrocarbon gas mixture whereby to transfer methanol values from said aqueous stream to said hydrocarbon stream.

Where a boiling liquid is employed as coolant, the heat exchanger preferably includes means for returning gas recovered from the outlet of said first passageway downwardly through the heat exchanger in indirect heat exchange relationship with the composition passing up said first passageway and between said first passageway and said second passageway.

In a preferred embodiment, the apparatus includes means for effecting indirect heat exchange between said composition and condensate falling back from said first passageway inlet to said separator through said first conduit means before said composition enters said first passageway inlet.

The invention also provides a tanker ship including apparatus for simultaneously cooling and dehydrating a gaseous composition comprising a water-containing hydrocarbon gas mixture and methanol vapour and obtaining a chilled condenate from said gas mixture eventual storage in a cargo space of said tanker, said apparatus comprising a heat exchanger having at least a first passageway adapted for generally upward passage therethrough of said composition from an inlet at the bottom to an outlet at the top and generally countercurrent downward passage therein to the inlet of condensate formed in said passageway from said composition and at least a second passageway adapted for passage therethrough of a coolant in indirect heat exchange relationship with said composition in said first passageway to cool said composition as it passes upwards from said inlet to said outlet; means for supplying said composition to said inlet; a gas/liquid separator; conduit means connecting the gas space in said separator with the inlet of said first passageway and adapted to pass gas from said space generally upwardly to said passageway inlet and permit condensate formed in said passageway to fall back from said inlet to said separator, said separator also having first and second outlets for a hydrocarbon phase and an aqueous phase, respectively, of said condensate; and means for transferring hydrocarbon liquid from said first outlet to said cargo space.

The apparatus on the tanker may further include mixing means for intimately mixing hydrocarbon liquid from said first separator outlet with an aqueous methanol solution, cooling the resultant mixture and separating it into a hydrocarbon phase and aqueous phase and passing the last-mentioned hydrocarbon phase to said cargo space, and optionally also means for reducing the pressure of said last mentioned hydrocarbon phase whereby a portion thereof is vaporized to form a second gaseous composition comprising a water-containing gas mixture and methanol vapour and including a second apparatus of the reflux heat exchanger kind as defined above for cooling and partially condensing said second composition and returning the condensate to a cargo space.

The apparatus of the invention may also be provided on an off-shore installation such as a moving platform or barge or tower loading buoy, in which case it may include means for transferring hydrocarbon liquid from the gas/liquid separator to a means for dispensing the liquid into a cargo space of a tanker ship.

The invention will now be described in more detail with reference to preferred embodiments thereof and with the aid of the accompanying drawings in which:

FIG. 1 is a diagrammatic flow sheet of one arrangement in accordance with the invention for treating a gas comprising a water-containing gaseous hydrocarbon mixture and methanol;

FIG. 2 is a modification of the arrangement shown in FIG. 1 in which the heat exchanger is adapted for use with a boiling liquid refrigerant;

FIG. 3 is a modification of the arrangement shown in FIG. 2;

Figure 4:
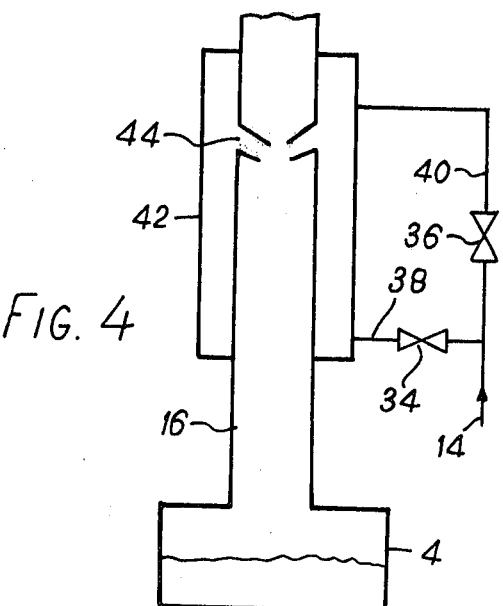
FIG. 4 shows a modification of the arrangement under the heat exchanger of FIGS. 1, 2 or 3, which modification is particularly suitable where simultaneous partial condensate of the gaseous hydrocarbon mixture is required.

In all Figures, the heat exchanger is shown with the passageways vertical. However they may also be inclined to the vertical, although preferably by an angle of not more than 45°.

Referring to FIG. 1, reference numeral 2 is a mixing or dispersing device, 4 is a gas/liquid separator and 6 is a heat exchanger. A gaseous hydrocarbon mixture containing water and which is to be cooled or chilled is passed via pipeline 10 to the mixing or dispersing device 2. The mixing or dispersing device may be a spray chamber, a packed column, a bubbling device or some such similar device in which a controlled amount of methanol either as such or as an aqueous solution thereof may be added through pipeline 12 to the incoming gas stream. Alternatively the gas in pipeline 10 may come from a prior process or separator in which methanol has been incorporated into the gas such that additional methanol need not be added in the mixing device or dispersing device 2 which is merely employed to effect intimate mixing or dispersing of the methanol in the gas or may be discarded if intimate mixing has already taken place. Such an alternative scheme would be where the gas comprises boil-off gases from a tank containing refrigerated gas liquids to which methanol has been added to permit the gas liquids to be cooled to the storage temperature without the formation of ice or hydrate by any water present in them.

Gas from the mixing or dispersing device 2 and containing a controlled amount of methanol vapour passes via pipeline 14 to the gas/liquid separator 4.

The gas may contain hydrocarbons which are to be condensed and stabilized as well as water vapour which is to be removed down to a temperature at or below the hydrate or ice formation temperature of the incoming hydrocarbon gas mixture.

The gas passes from the gas/liquid separator 4 upwards via the pipeline, or gas passage, 16 which may be in effect a multiplicity of such passages such as the extended tubes of a vertical shell and tube heat exchanger. As will be shown, the gas passing upward through 16 flows counter-current to downward flowing condensate from the heat exchanger 6. Gas from 16 passes into the tubes or passageways of heat exchanger 6, one of which is illustrated and identified by reference numeral 18. The passageways 18 will generally be the tubes of a shell and tube heat exchanger or passageways in a plate and fin exchanger or some such similar heat exchanger device offering vertical heat exchange surfaces such that gas may pass upwards in close contact with liquid condensate passing down the walls of the heat exchange surfaces. The device illustrated in FIG. 1 is a section of a plate and fin exchanger. As the gas passes up through 18, it is cooled and its temperature progressively decreased. Condensate carrying condensed hydrocarbons, water and methanol flows down the tube counter-current to the upflowing gas. This has the effect of stabilising the down-flowing liquid, to remove light hydrocarbons in preference to heavier hydrocarbons from the down flowing liquid and to remove water vapour in preference to methanol vapour from the up flowing gas. Therefore the gas at the top has a higher methanol:water ratio than at the inlet and can withstand a lower temperature without ice or hydrate formation than would be possible in a conventional heat exchanger. Condensate passes down the walls of pipe or passageway 18 and thence via pipe or passageway 16 to the gas liquid separator 4 where it is drawn off via pipeline or duct 26 for subsequent separation into aqueous and hydrocarbon phases and utilization of the recovered hydrocarbon phase e.g. by shipment at sub-ambient temperature in a refrigerated tanker ship and consumption at a remote location, e.g. as feed for a steam cracker.

Cold gas leaves the top of passageway 18 depleted in condensate and is passed via transfer pipe or duct 20 to the heat exchanger pipe or passageway 22 where it flows downward by counter-current to the gas flow in the pipe or passageway 18 and extracts heat from the gases in 18. It is then recovered via pipe or duct 24.

In the embodiment shown in FIG. 1, the necessary refrigeration for the heat exchanger 6 is provided by a cooled stream which in this case is a refrigerated gas entering via pipeline or duct 28 and thence to duct or passageway 30 in which it flows downwardly counter-currently to the gas flow in duct or passageway 18, extracting heat from the gases in 18. It is then withdrawn from the heat exchanger via pipe or duct 24. The refrigerated gas may be provided from an external refrigeration loop using for example a compressor and expansion turbine or may be derived by externally cooling the gas from duct 24 in a refrigerator heat exchanger or if the gas recovered in duct 24 is at a suitably elevated pressure it may be derived by expanding gas from duct 24 in an expansion turbine to a suitable pressure and passing the gas to duct 28. Other schemes will occur to those skilled in the art as suitable to provide the refrigerated gas.

If a boiling liquid refrigerant is employed as the cooling medium, it is preferred not to use it directly as outlined in the above description. It is not desirable to use a boiling liquid refrigerant directly against the wall of the passageway or duct 18 carrying the upward flowing gas to be cooled. This is because the heat exchange coefficients for boiling refrigerants are very high and therefore the heat exchange surface in contact with this liquid refrigerant would tend to have a more uniformly cold temperature than would be the case where a cold gas is used as the refrigerant. It is preferred that there be a reasonably uniform temperature drop in the heat exchange surface in contact with down-flowing condensate and up-flowing gas in the passageway 18 so that the minimum amount of methanol is required in order to prevent freezing or hydrate formation on the tube wall.

A further embodiment of the invention will now be described by way of example with reference to the accompanying FIG. 2 in which, as in FIG. 1, reference numeral 4 is a gas liquid separator and 6 is a heat exchanger of the plate and fin type. In this embodiment, however, the exchanger has two parallel heat exchange clusters. This arrangement permits the use of a boiling liquid refrigerant in the heat exchanger without causing excessive cooling and a uniform temperature of the walls next to the gas to be treated.

The gas to be treated enters via pipeline or duct 14 and passes to the gas liquid separator 4 and then, as in FIG. 1, via duct or ducts 16 into the passageways 18 in the heat exchanger block. The gas passes upward in the passageways 18 which can be formed by vertical plain or slotted corrugated plates between the flat spacer plates in the heat exchanger or alternatively by special plates such as overflow packing or alternative designs of plate which ensure that the condensate formed from the rising gas flows downward wetting the walls of 18 in counter-current flow with the rising gas. Cooled gas from the tops of the passageways 18 is passed to the transfer duct or header, 20 and thence is passed back downwards through the heat exchanger in the passageways 22 leaving the exchanger through outlet duct or header 24.

Boiling liquid refrigerant to provide the refrigeration load enters the heat exchange block via duct or header 28 and passes to passageways 30 which are adjacent to passageways 22 but not adjacent to passageways 18. Whilst the refrigerant ducts may extend the whole length of the block and the refrigerant, with careful liquid distribution, might be allowed to flow downward in true counter-current flow, the arrangement shown is the normal upward flow in which total evaporation is not essential and where the liquid in header 32 may be recovered and returned with fresh refrigerant to duct or header 28. In this arrangement the refrigerant is isolated from direct proximity to the gas being chilled and treated in passageway 18 by the gas passageways 22 and in this way the temperature profile through the walls of the passageways 18 is kept such that the walls become progressively cooler up the heat exchanger and do not undergo the sudden cooling which would occur if the boiling liquid refrigerant were in direct contact with the walls of the passageways 18.

It should be noted that whereas FIGS. 1 and 2 show the gas to be treated being cooled to the required treatment temperature and thereafter being reheated by heat exchange with the incoming gas prior to being discharged, the same treatment system may also be used without the step of reheating the gas in passageway 22. Such an arrangement may be desirable, for example, in the case of treatment of natural gas prior to passing it onwards to a liquefaction stage to produce LNG. In this case the treated gas leaving passageways 18 at the top of the exchanger may pass onward and not back via duct or passageways 22. Where a boiling liquid refrigerant is used and where it is desirable not to overchill the heat transfer surfaces of passageways 18, the scheme shown in FIG. 3 may be used. In this arrangement, chilled and treated gas leaving passageways 18 passes via duct or header 20 into passageways 22 and thence counter-current to the gas flow in 18 leaving via duct or header 25 and into passageway 23 which passes on the other side of 18 upward and co-current with the gas flow 18 with the gas leaving the top of the exchanger via duct or header 24. The gas is thus recovered from the cold end of the exchanger.

Where the gas to be treated comprises a multi-component mixture of compounds some of which are to be condensed and removed by chilling; e.g. a gas liquids fraction in a natural gas stream, the liquids leaving the heat exchanger as shown in FIGS. 1 and 2 are stabilized but nevertheless are in equilibrium with the incoming gas and may thus still contain some undesirable light fractions. These may be removed by separate flashing or distillation steps or alternatively they may be rectified employing the arrangement shown in FIG. 4.

In FIG. 4, as in FIGS. 1 and 2, reference numeral 4 is a gas liquid separator. Similarly, passageway or duct 16 is a multiplicity of passageways or ducts leading to the heat exchanger 6 of FIG. 1, 2 or 3 and may be continuations of the passageways 18 shown in FIGS. 1 and 2.

As in FIGS. 1, 2 and 3, gas flows upward in 16 and condensed liquid flows down the walls of the passageways. An opening or openings 44 are located near the top of 16 near where it passes upwards and becomes passageway 18 of the heat exchanger. The openings 44 are arranged such as to allow ingress of gas in to the passageway 16 without escape of liquid from passageway 16 into 42 which is a heat exchange area of passageway adjoining the passageway 16. If the unit is a shell and tube heat exchanger, 42 may be a shell zone separated from passageways 22 and 30 (see FIG. 1) by a tube plate. If the unit is a plate and fin unit as shown in FIGS. 1, 2 and 3, 42 may be gas passages at the bottom of the exchanger adjacent to 16 with 16 being a continuation of 18 and with passageway 42 being isolated from the passageways 22, 23 and 30 shown in FIGS. 1, 2 and 3.

Hot incoming gas to be treated enters the system in duct or passageways 14 and is directed into the base of passageway 42 or by-passed to the top of passageway 42 by means of valves 34 and 36 and ducts or passageways 38 and 40 respectively. Hot gas entering via valve 34 and passageway or duct 38 into 42 heats the liquid flowing down the walls of passageway 16 and boils off undesirable light fractions in the liquid. Passageway 16 thus acts as a distillation column with the removed light gases passing upwards to join the incoming gas which enters passageway 16 via the openings 44 before passing to the duct or passageways 18 (as shown in FIGS. 1, 2 and 3) for cooling in heat exchanger 6 (see FIGS. 1, 2 and 3). The degree of removal of light fraction in 16 may be controlled by the direction or by-passing of hot incoming gas via valves 34 and 36 to the base or top of 42.

Where the chilling causes partial condensation of the hydrocarbon mixture, the condensate removed will be in two phases; a hydrocarbon phase and an aqueous phase. Because this invention allows the reduced usage of methanol for a given duty, the water content of the methanol-water condensate recovered from the gas will be higher than with conventional treatment and as a result the solubility and loss of methanol in the hydrocarbon phase is reduced. The aqueous and hydrocarbon phase may be separated and at least part of the methanol in the aqueous phase may be recovered and recirculated for injection into the incoming gas. An arrangement for such a technique is shown in FIG. 5.

Figure 5:
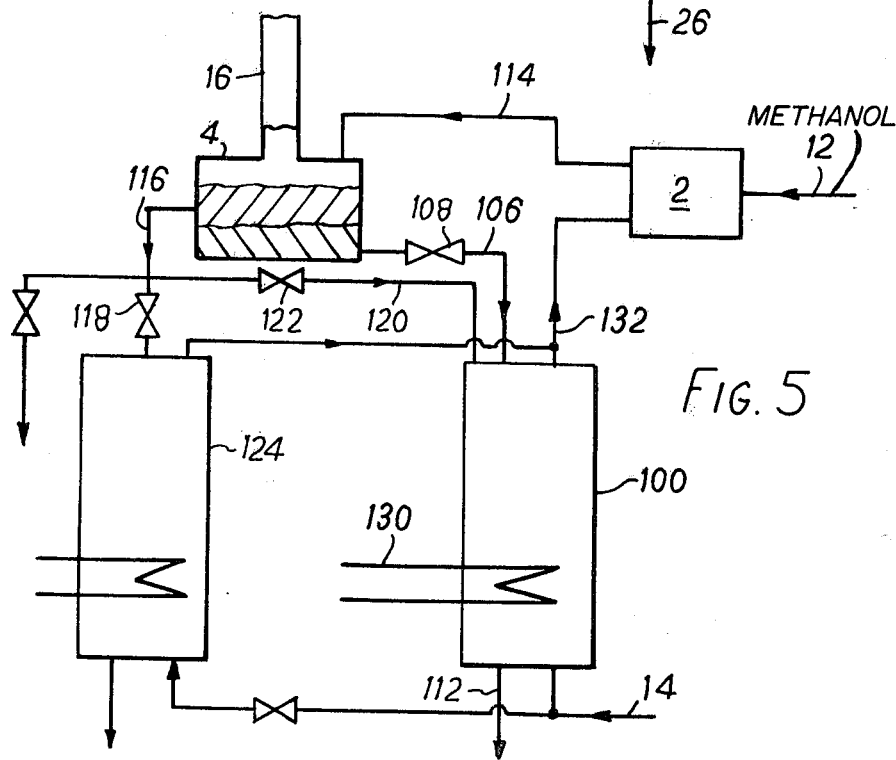
FIG. 5 shows an arrangement which permits recovery of at least some of the methanol condensed from the gas and recycle of the reclaimed methanol for admixture with fresh gas.

In FIG. 5, 2 is a mixing device as described for FIG. 1, 4 is a three phase gas/hydrocarbon liquid/aqueous phase separator, 100 is a contacting device such as a spray tower, packed tower, bubble cap tower, or similar device, and 130 is a heating device such as a heating coil, element, exchanger or similar device.

In this arrangement, condensate falling back down passageway 16 as described with reference to FIGS. 1, 2, 3 and 4 passes to the separator 4 in which it separates into a lower aqueous phase and upper hydrocarbon phase. The upper hydrocarbon phase is drawn off via line 116 and valve 118 and may be disposed of as such or further stabilised or treated by conventional means.

The lower aqueous phase containing the bulk of the recovered methanol is drawn off via line 106 and valve 108 and may subsequently be distilled by conventional means to recover the methanol or may, as shown in FIG. 5, pass to a contacting device in which the incoming gas to be treated in heat exchanger 6 (FIGS. 1, 2 and 3) enters at the bottom via pipeline or duct 14 and contacts the aqueous liquid and preferentially strips methanol from said liquid before leaving via pipeline 132 and passing to the mixing device 2 where make-up methanol is added as required via pipeline 12 before the finally treated gas passes via pipeline 114 to the gas liquid separator 4 and then via duct or passageway 16 for treatment as described with reference to FIGS. 1, 2, 3 or 4.

Further rectification of the liquid hydrocarbon phase recovered through pipeline 116 may be achieved by countercurrently contacting it, either in contacting device 100 to which it is supplied via line 120 and valve 122, or in a separate contacting device 124, with the feed gas mixture entering in line 14.

While the invention has been described and illustrated with reference to a single refluxing heat exchanger and a single draw-off point for condensate formed in the heat exchanger, several such heat exchange steps may be provided in series to produce a plurality of condensates when partial condensation of the gaseous hydrocarbon mixture is effected. Other processing operations may be interspersed between the heat exchange steps. For example, the process is particularly well suited to pre-treating a natural gas or associated gas prior to a low temperature methanol or methanol/water wash to remove acid gases.

One particularly important application of the process is for the recovery at superatmospheric pressure of a liquid fraction consisting predominantly of hydrocarbons selected from $C_2$–$C_4$ hydrocarbons and mixtures thereof from a wet associated gas or natural gas stream, with simultaneous dehydration of the gas stream.

Figure 6:
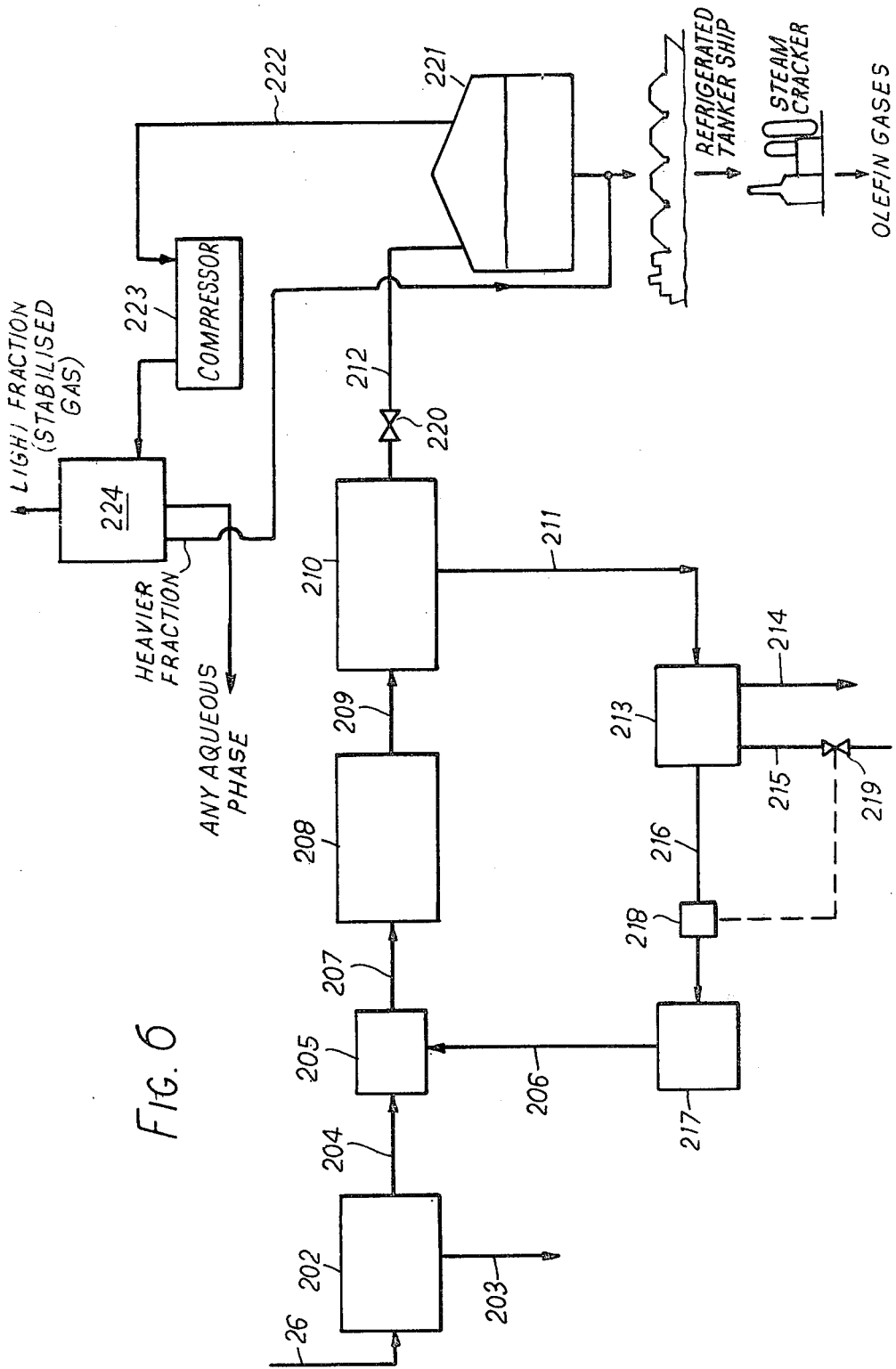
FIG. 6 is a diagrammatic flow sheet of an arrangement particularly suitable for the production of a liquid hydrocarbon fraction suitable for subsequent transport to a remote location for conversion to olefin gases by steam cracking.

The liquid fraction thereby obtained is particularly suitable for conversion to olefin gases by steam cracking. However, it will generally still contain some water and thus where the steam cracking facility is geographically remote from the location where the fraction is formed and it is necessary to transport the fraction at a sub-zero temperature in a tanker, it may be necessary to remove more water from the fraction. This may conveniently be achieved by means of the arrangement and apparatus now described with reference to FIG. 6. After the liquid hydrocarbon fraction in condensate recovered, e.g. in line 26 of the apparatus of any of FIGS. 1–4 has been separated from the co-condensed aqueous phase in liquid/liquid separator 202, the aqueous phase being withdrawn through line 203, said liquid fraction is passed through line 204 to be intimately mixed in mixing means 205 with an aqueous solution of methanol which is substantially insoluble in the fraction and has a freezing point below the temperature to which the mixture is to be cooled in cooler 208 and which is provided through line 206. The mixture thus obtained is then passed via line 207 to cooler 208 where it is cooled so that water in the fraction is absorbed preferentially in the aqueous methanolic solution and a hydrocarbon phase and aqueous methanol phase are formed. The cooled mixture thus obtained is passed via line 209 to separator 210 where the hydrocarbon phase is separated from the aqueous phase. Preferably, at least part of the aqueous phase, which is recovered through line 211, is recycled via line 216 and circulation pump 217 to be mixed with fresh liquid fraction, the methanol concentration of the recycling liquor being continuously or intermittently restored towards that of the aqueous solution initially employed and the inventory of said liquor continuously or intermittently restored towards its initial level, e.g. by means of purge/make-up device 213 where make-up methanol is supplied through line 215 and excess liquor is removed through line 214. This process with recycle of the aqueous phase forms the subject of copending application Ser. No. 054,418, filed July 3, 1979, particularly FIG. 2 thereof.

The chilled hydrocarbon fraction thereby obtained and which is recovered through line 212 will generally still be at a superatmospheric pressure and a portion of it will vaporise when it is let down to about atmospheric pressure, e.g. through valve 220 for storage and or transport. The gas thereby produced, and which will still contain water vapour up to saturation point at the prevailing temperature and pressure, and some methanol, is separated from the liquid, e.g. in gas/liquid separator 221, and is normally thereafter recompressed, e.g. in compressor 223 to which it is supplied in line 222, and separated into a light fraction which is vented, stored or used as fuel, and a heavier fraction which it is desired to recover and return to mix with the remainder of the chilled fraction. The compression step, however, increases the water vapour pressure and it is therefore desirable to remove more water from the compressed gas. Conveniently, this may be achieved simultaneously with the separation step by using the process of the present invention, e.g. by passing the compressed gas to unit 224 which may be an apparatus as described with reference to any of FIGS. 1-5.

All the above steps of recovering and subsequently treating the liquid fraction can be operated using apparatus which is compact and which is relatively unaffected by movement or tilting and which can thus be installed on moving platforms, ships, barges or tower loading buoys. There is thus provided a valuable overall method of obtaining from a natural or associated gas from an offshore source, a hydrocarbon material which is particularly suitable for conversion to valuable olefin gases by steam cracking at a location which is geographically remote from the point of supply of the material and to which the material is transferred at least in part by transport at sub-zero temperature in a tanker ship.

The invention will now be illustrated by way of the following Example.

EXAMPLE

The exchanger consisted of a bundle of 5 parallel tubes formed from ⅜ inch o.d. tubing, arranged with a central tube surrounded by and soldered to the other 4. The central tube was formed to change its cross-sectional shape from circular to parallel sided with semicircular ends, the radius of the ends being 3/32 inch and the overall length and width of the tube being ⅜ inch and 3/16 inch respectively (internal dimensions). Two of the outer tubes were formed to have flat sides to fit alongside the parallel flat sides of the central tube, and the remaining two were formed to adopt a kidney shape in cross-section to fit round the semicircular ends of the central tube. Each outer tube was 6 ft long; the inner tube was 6 ft 8 inches long with 8 inches extending downwardly from the bottom of the bundle into a receiver which had an inlet for the gas to be treated and a drain leading to a second vessel where recovered liquid separated into aqueous and hydrocarbon phases.

The gas to be treated passed upwards through the central tube and cooling was provided by passing refrigerated gaseous Freon 502 downwards through the outer tubes. Thermocouples measuring the outside wall temperature of the central tube and gas sampling points were provided at top, mid-point and bottom of the bundle.

The feed supplied to the central tube was the product of contacting a gaseous methane, ethane, propane and butane mixture with an aqueous methanol solution. The feed had a composition A and was supplied at a temperature B, and a pressure C. Product gas was recovered from the top of the tube at a flow rate D.

The bottom, mid-point and top temperatures of the tube (outside wall temperatures as measured by the thermocouples) were E, F and G.

Samples of the gas in the central tube were taken at the bottom and the top of the tube and were found by gas chromatographic analysis to have compositions H and J respectively.

After K of gas had been recovered from the top of the tube, the condensate recovered from the bottom of the central tube of the column was found to comprise L of aqueous phase of composition M and N of hydrocarbon phase of composition P.

In a comparative experiment where the feed gas is cooled by conventional means with co-current flow of gas and condensate formed from the gas by the cooling, hydrate and ice formation occur at or above R. If ice and hydrate formation is suppressed by adding more methanol, S of hydrocarbon condensate having a composition T is obtained after treating the same amount of feed as above.

The values for A to T are given below.

|   |   | Mole % | | | | | |
|---|---|---|---|---|---|---|---|
|   |   | $C_1$ | $C_2$ | $C_3$ | $C_4$ | $CH_3OH$ | $H_2O$ |
| A | feed gas composition | 0.55 | 39.88 | 56.15 | 2.34 | 0.06 | 1.02 |
| H | Gas composition at bottom of tube | 0.55 | 52.98 | 44.55 | 1.57 | 0.10 | 0.25 |
| J | Gas composition at top of tube | 2.51 | 95.76 | 1.63 | <0.1 | 0.10 | <0.01 |
| M | Composition of recovered liquid aqueous phase | <0.1 | <0.1 | <0.1 | <0.1 | 3.6 | 96.4 |

-continued

|   |                                                    |       |       |       |      |       |       |
|---|----------------------------------------------------|-------|-------|-------|------|-------|-------|
| P | Composition of recovered liquid hydrocarbon phase  | <0.1  | 24.65 | 72.32 | 3.03 | <0.1  | <0.1  |
| T | Composition of condensate obtained by conventional treatment | 0.56 | 40.32 | 56.75 | 2.37 | —     | —     |

| | | |
|---|---|---|
| B | Feed Gas Temperature | 31.5° C. |
| C | Feed Gas Pressure | 14.6 atma |
| D | Product Gas Flow Rate | 79.3 liters/hr |
| E | Tube Bottom Temperature | 13.5° C. |
| F | Tube Mid-Point Temperature | −10° C. |
| G | Tube Top Temperature | −19.5° C. |
| K | Quantity of Gas recovered from Tube Top | 304 normal liters. |
| L | Quantity of Liquid Aqueous Phase recovered | 12 ml |
| N | Quantity of Liquid Hydrocarbon Phase recovered | 4080 ml |
| R | Hydrate/ice formation temperature for conventional cooling | −6.4° C. |
| S | Amount of gas condensed using conventional cooling | 100%. |

It will thus be seen that under the conditions employed substantially all the $C_3$ in the feed gas is recovered in the condensate and no freezing occurs. However if conventional cooling had been used, freezing would have occurred less than half way along the heat exchanger and if this had been suppressed by adding more methanol all the gas would have condensed and no separation would have occurred.

We claim:

1. A method of simultaneously dehydrating and chilling a gaseous composition comprising a water-containing gaseous hydrocarbon mixture and a controlled or known concentration of methanol vapour to a temperature which lies below the ice or hydrate formation temperature of said water-containing gaseous hydrocarbon mixture by passing it upwards in indirect heat exchange relationship with a coolant through a heat exchanger in which the composition is cooled and liquids therefrom flow downwards in a counter-current fashion in contact with the rising composition being cooled, the temperature of the rising composition and the down flowing condensed liquids in the exchanger decreasing from bottom to top of the heat exchanger, and recovering a dehydrated hydrocarbon gas from the top of the exchanger and an aqueous condensate from the bottom.

2. A method as claimed in claim 1 in which prior to entering the heat exchanger the composition is passed in indirect heat exchange relationship with condensed liquids recovered from the lower end of the heat exchanger, to further rectify said liquids.

3. A method as claimed in claim 1 in which at least some of the aqueous phase recovered from the lower end of the heat exchanger is contacted with fresh aqueous hydrocarbon mixture containing water prior to the latter entering the heat exchanger, said contacting being effected at a temperature at which at least some of the methanol in said aqueous phase is vaporized from said phase and entrained in said fresh aqueous hydrocarbon mixture to form a gaseous composition containing said gaseous hydrocarbon mixture, water and a controlled or known concentration of methanol vapour.

4. A method as claimed in claim 1 in which the gaseous hydrocarbon mixture is partially condensed by said chilling and the condensate recovered from the bottom of the heat exchanger is separated into an aqueous phase and a liquid hydrocarbon phase.

5. A method comprising discharging from the cargo space of a tanker ship, a product obtained by the method of claim 4 and which product has been transported at least in part at subambient temperature in the cargo space of the tanker ship.

6. A method as claimed in claim 4 in which the liquid hydrocarbon phase is countercurrently contacted with the gaseous composition prior to the latter entering the heat exchanger.

7. A method as claimed in claim 4 in which the gaseous hydrocarbon mixture comprises a natural gas or associated gas and the chilling is effected at superatmospheric pressure to separate from said gas a condensed liquid fraction consisting predominantly of hydrocarbons selected from $C_2$ to $C_4$ hydrocarbons and mixtures thereof.

8. A method as claimed in claim 7 in which said liquid fraction is intimately mixed at superatmospheric pressure with an aqueous solution of methanol and then cooled whereby water in the fraction is absorbed preferentially into the aqueous methanolic solution and a hydrocarbon phase and aqueous methanol phase are formed, and the hydrocarbon phase is separated from said aqueous phase, the aqueous solution being substantially insoluble in the liquid fraction and have a freezing point below the temperature to which the mixture is cooled.

9. A method as claimed in claim 8 in which at least part of said aqueous phase is recycled to be mixed with fresh liquid fraction, the methanol concentration of the recycling liquor being continuously or intermittently restored towards that of the aqueous solution initially employed and the inventory of said liquor continuously or intermittently restored towards its initial level.

10. A method as claimed in claim 8 in which the pressure of the hydrocarbon phase separated from the aqueous phase is reduced and the vapours thereby generated are recompressed and thereafter simultaneously dehydrated and chilled by the method claimed in claim 4 to separate them into a gaseous light fraction and a condensed heavier fraction which is returned to be mixed with the hydrocarbon phase at said reduced pressure.

11. A method of producing olefinic gases from a light hydrocarbon feedstock obtained from a water-containing gaseous hydrocarbon mixture and at a location which is geographically remote from the point of supply of said mixture, the method comprising steam cracking at said location a light hydrocarbon feedstock comprising a liquid fraction consisting predominantly of hydrocarbons selected from $C_2$–$C_4$ hydrocarbons and mixtures thereof, said fraction having been derived from the condensate obtained by treating said mixture by the method claimed in claim 4 and having been thereafter transferred to said location at least in part by transportation at sub-ambient temperature in a tanker ship.

12. A method as claimed in claim 11 in which said mixture is selected from wet natural gas and wet associated gas.

13. A method as claimed in claim 11 wherein said fraction is provided at said sub-ambient temperature from said condensation for transportation by intimately mixing said condensate at superatmospheric pressure with an aqueous solution of methanol and then cooling it whereby water in the condensate is absorbed preferentially into the aqueous methanolic solution and a hydrocarbon phase and aqueous methanol phase are formed and recovering the hydrocarbon phase, the aqueous solution being substantially insoluble in the condensate and having a freezing point below the temperature to which the mixture is cooled.

14. A tanker ship including apparatus for simultaneously cooling and dehydrating a gaseous composition comprising a water-containing hydrocarbon gas mixture and methanol vapour and obtaining a chilled condensate from said gas mixture for eventual storage in a cargo space of said tanker, said apparatus comprising a heat exchanger having at least a first passageway adapted for generally upward passage therethrough of said composition from an inlet at the bottom to an outlet at the top and generally countercurrent downward passage therein to the inlet of condensate formed in said passageway from said composition and at least a second passageway adapted for passage therethrough of a coolant in indirect heat exchange relationship with said composition in said first passageway to cool said composition as it passes upwards from said inlet to said outlet, means for supplying said composition to said inlet; a gas/liquid separator; conduit means connecting the gas space in said separator with the inlet of said first passageway and adapted to pass gas from said space generally upwardly to said passageway inlet and permit condensate formed in said passageway to fall back from said inlet to said separator, said separator also having first and second outlets for a hydrocarbon phase and an aqueous phase, respectively, of said condensate; and means for transferring hydrocarbon liquid from said first outlet to said cargo space.

15. A tanker ship as claimed in claim 14, including means for intimately mixing hydrocarbon liquid from said first separator outlet with an aqueous methanol solution, cooling the resultant mixture and separating it into a hydrocarbon phase and an aqueous phase and passing the last-mentioned hydrocarbon phase to said space.

16. A tanker ship as claimed in claim 15 further including means for reducing the pressure of said last-mentioned hydrocarbon phase whereby a portion thereof is vaporised to form a second gaseous composition comprising a water-containing gas mixture and methanol vapour and including a second apparatus as defined in claim 13 for cooling and partially condensing said second composition and returning the condensate to a cargo space.

17. Apparatus for simultaneously cooling and dehydrating a water-containing gaseous hydrocarbon stream, the apparatus including a mixer for mixing methanol with said stream and having inlets for a methanol-containing stream and said hydrocarbon stream and an outlet for the gaseous composition formed by mixing said stream; a heat exchanger having at least a first passageway adapted for generally upward passage therethrough of said composition from an inlet at the bottom to an outlet at the top and generally countercurrent downward passage therein to the inlet of condensate formed in said passageway from said composition and at least a second passageway adapted for passage therethrough of a coolant in indirect heat exchange relationship with said composition in said first passageway to cool said composition as it passes upwards from said inlet to said outlet; means for supplying said composition from said mixer outlet to said heat exchanger passageway inlet; a gas/liquid separator having at least one outlet for liquid collected therein; and conduit means connecting the gas space in said separator with the inlet of said first passageway and adapted to pass gas from said from said space generally upwardly to said passageway inlet and permit condensate formed in said passageway to fall back from said inlet to said separator.

18. Apparatus as claimed in claim 17, including means for effecting indirect heat exchange between said composition and condensate falling back from said first passageway inlet to said separator through said first conduit means before said composition enters said first passageway inlet.

19. Apparatus as claimed in claim 17 installed on board a tanker ship and including means for transferring hydrocarbon liquid from said separator to a cargo space of a tanker ship.

20. Apparatus as claimed in claim 17 forming part of an off-shore installation and including means for transferring hydrocarbon liquid from said separator to a dispensing means for dispensing the liquid into a cargo space of a tanker ship.

21. Apparatus for simultaneously cooling and dehydrating a gaseous composition comprising a water-containing hydrocarbon gas mixture and methanol vapour and obtaining a chilled condensate from said gas mixture, e.g. for eventual storage in a cargo space of a tanker, said apparatus comprising a heat exchanger having at least a first passageway adapted for generally upward passage therethrough of said composition from an inlet at the bottom to an outlet at the top and generally countercurrent downward passage therein to the inlet of condensate formed in said passageway from said composition and at least a second passageway adapted for passage therethrough of a coolant in indirect heat exchange relationship with said composition in said first passageway to cool said composition as it passes upwards from said inlet to said outlet, means for supplying said composition to said inlet; a gas/liquid separator; conduit means connecting the gas space in said separator with the inlet of said first passageway and adapted to pass gas from said space generally upwardly to said passageway inlet and permit condensate formed in said passageway to fall back from said inlet to said separator, said separator also having first and second outlets for a hydrocarbon phase and an aqueous phase, respectively, of said condensate; and means for contacting an aqueous stream from said aqueous phase outlet with said water-containing hydrocarbon gas mixture whereby to transfer methanol values from said aqueous stream to said hydrocarbon stream and supply the resultant methanol containing composition to said first passageway inlet of said heat exchanger.

22. Apparatus as claimed in claim 21, including means for effecting indirect heat exchange between said composition and condensate falling back from said first passageway inlet to said separator through said first conduit means before said composition enters said first passageway inlet.

23. Apparatus as claimed in claim 21 installed on board a tanker ship and including means for transferring hydrocarbon liquid from said separator to a cargo space of a tanker ship.

24. Apparatus as claimed in claim 21 forming part of an off-shore installation and including means for transferring hydrocarbon liquid from said separator to a dispensing means for dispensing the liquid into a cargo space of a tanker ship.

* * * * *